United States Patent [19]

Dubois et al.

[11] Patent Number: 4,583,283
[45] Date of Patent: Apr. 22, 1986

[54] ELECTRICALLY ISOLATED SEMICONDUCTOR POWER DEVICE

[75] Inventors: Jerry M. Dubois, Mesa; Keith G. Spanjer, Scottsdale, both of Ariz.

[73] Assignee: Motorola, Inc., Schaumburg, Ill.

[21] Appl. No.: 693,695

[22] Filed: Jan. 22, 1985

Related U.S. Application Data

[62] Division of Ser. No. 362,273, Mar. 26, 1982, Pat. No. 4,510,519.

[51] Int. Cl.$^4$ .............. H01L 23/02; H01L 23/30; H01L 29/06
[52] U.S. Cl. ........................... 29/589; 29/571; 29/580; 148/1.5; 357/81; 357/73; 357/80; 357/55
[58] Field of Search .............. 29/571, 578, 580, 589, 29/590; 148/1.5; 357/81, 73, 80, 55

[56] References Cited

U.S. PATENT DOCUMENTS

| | | | |
|---|---|---|---|
| 3,902,148 | 8/1975 | Drees et al. | 357/69 X |
| 3,946,428 | 3/1976 | Anazawa et al. | 357/84 X |
| 4,278,990 | 7/1981 | Fichot | 357/81 |
| 4,278,991 | 7/1981 | Ritchie et al. | 357/81 |
| 4,340,900 | 7/1982 | Goronkin | 357/81 X |
| 4,450,471 | 5/1984 | Wellhoefer et al. | 357/80 |
| 4,510,519 | 4/1985 | Dubois et al. | 357/81 |

*Primary Examiner*—Brian E. Hearn
*Assistant Examiner*—David A. Hey
*Attorney, Agent, or Firm*—Robert M. Handy

[57] ABSTRACT

An improved power semiconductor device and manufacturing method are described wherein the external, thermally conducting, heat transfer face of the device is electrically insulated by a glassy dielectric which is intimately bonded directly to the conductive heat spreader supporting the semiconductor die. By forming the exposed corners of the heat spreader to be substantially smooth curved surfaces having a predetermined minimum radius of curvature greater than the thickness of the glassy dielectric, formation of a ridge of glass at the corners and edges of the heat spreader is avoided. For ease of assembly the piece parts are initially substantially flat and parallel. A molding compound of controlled shrinkage is used to avoid distorting the substantially flat smooth insulated heat transfer face which remains exposed in the encapsulated device.

8 Claims, 12 Drawing Figures

ELECTRICALLY ISOLATED SEMICONDUCTOR POWER DEVICE

This is a division, of application Ser. No. 362,273, filed Mar. 26, 1982 now U.S. Pat. No. 4,510,519.

BACKGROUND OF THE INVENTION

1. Field of the Invention

This invention relates to, in general, improved semiconductor devices and, more particularly, to packages for high power semiconductor devices having an insulated heat spreader adapted to be thermally coupled to but electrically isolated from an external heat sink.

2. Background Art

Power semiconductor devices must dissipate substantial amounts of heat. To accomplish this they are typically provided with metallic heat spreaders which are adapted to couple directly to an external heat sink. The semiconductor die within the device are usually mounted directly on the heat spreader in order to obtain the most efficient heat transfer to the external heat sink. As a consequence the heat spreader is electrically coupled to the semiconductor die. As used herein, the words "heat spreader" refer to the thermally and electrically conductive member which is the principal heat extraction pathway between the heat source and the external heat sink.

In many applications, the semiconductor die must be at one electrical potential while the external heat sink is at a different electrical potential. In the prior art, two approaches have been taken to provide electrical isolation of the semiconductor chip while still maintaining some degree of thermal coupling to the external heat sink. These are: (1) inserting a thin ceramic isolator between the semiconductor chip and the heat spreader, or (2) placing a thin sheet of mica or plastic between the heat spreader and the external heat sink. The first of these approaches has the disadvantages of, (a) introducing a significant thermal impedance between the semiconductor die and the heat sink at the point of greatest thermal flux, and (b) significantly increasing manufacturing cost. The second approach suffers from the disadvantages that the mica or plastic sheet is, (a) a separate piece part which must be handled during mounting of the finished device to the external heat sink, thereby increasing the overall cost to the user, and (b) generally thicker, for ease of handling, than needed for electrical purposes, thereby increasing the thermal impedance. Thus, a need continues to exist for low cost power semiconductor devices and power semiconductor device packages in which the heat transfer face is electrically isolated from the semiconductor chip without substantial sacrifice in thermal performance, and which does not require the use of external isolators in mounting the device to the external heat sink.

Accordingly, it is an object of the present invention to provide an improved semiconductor power device in which the external heat transfer face is electrically isolated from the semiconductor die.

It is a further object of this invention to provide an improved semiconductor power device in which the external heat transfer face is electrically isolated from the semiconductor chip without the use of a dielectric spacer between the semiconductor chip and the heat spreader.

It is an additional object of this invention to provide an improved semiconductor power device adapted to provide electrical isolation between the semiconductor die and the external heat sink without the use of separate external insulating means.

It is a further object of this invention to provide an improved semiconductor power device in which electrical isolation is achieved by means of an insulating layer which is intimately bonded to the outward, heat transfer, face of the heat spreader.

It is a yet further object of the present invention to provide the above improved device in which the heat transfer face is substantially flat and smooth.

It is an additional object of this invention to provide an improved semiconductor power device which may be constructed with a minimum number of piece parts.

It is a further object of this invention to provide an improved semiconductor device wherein the piece parts are initially substantially flat to promote ease of assembly.

It is an additional object of this invention to provide an improved semiconductor device which is mechanically rugged and well adapted to the industrial environment.

It is a further object of the present invention to provide an improved method for the manufacture of power semiconductor devices and power semiconductor device packages having the above improved features.

SUMMARY OF THE INVENTION

The attainment of the foregoing and other objectives and advantages is achieved through the present invention wherein a metallic heat spreader is provided having a base portion of a first thickness and a lead portion of a second thickness. The base portion has a first surface, a second surface opposed to the first surface, and a side which is coupled to the first and second surfaces. On the first surface is a device mounting area and a lead mounting area. The side and the second surface are joined by a substantially smooth curved surface having a predetermined minimum radius. One or more additional leads are mechanically coupled to but electrically isolated from the lead mounting area of the first surface of the base portion of the heat spreader. A refractory dielectric coating is intimately bonded to the second surface of the base portion and to the substantially smooth curved surface joining the second surface to the side. The radius of curvature of the substantially smooth curved surface must be at least equal to or greater than the thickness of the refractory dielectric coating and desirably at least two to three times this thickness.

In further embodiments, the above described device is provided wherein the side has bends and/or corners along its length and in the direction of its length, none of which have a radius of curvature smaller than the thickness of the refractory dielectric coating, and preferably a radius of curvature several times this value.

Further, the additional leads are mechanically coupled to the base portion by means of a glassy or polymeric dielectric. At the point where the additional leads pass over the edge of the base portion, the base portion is notched to permit ready access of a bending tool so that the additional leads may be bent prior to encapsulation without damaging the polymeric or glassy attachment means or the refractory dielectric coating in the base portion. The base portion is also notched and relieved adjacent to the point where it joins the base lead portion. To facilitate handling and assembly, the base portion, the base lead portion, and the additional leads are initially substantially flat.

A method for manufacturing a power semiconductor device adapted to receive semiconductor die is provided, comprising: forming a metallic heat spreader having a base portion with a first surface adapted to receive semiconductor die, a second surface opposite the first surface adapted to receive refractory dielectric coatings, and a side portion coupled to the first and second surfaces; providing a base lead portion extending from the base portion and having a first extension portion ending in a first terminal portion; shaping the metallic heat spreader so that the base portion has a first thickness and the base lead portion has a second thickness; joining the side portion and the second surface by a substantially smooth surface having a predetermined minimum radius of curvature; attaching to the first surface of the base portion at least one additional lead having a second extension portion ending in a second terminal portion; and coating the second surface and a portion of the substantially smooth surface with a chemically bonded refractory dielectric material of predetermined thickness less than the predetermined minimum radius of curvature.

In further embodiments, the method includes; performing the coating step by applying a glass forming material, and simultaneously or sequentially heating to fuse the glass forming material and intimately bond it to the second surface and to a portion of the substantially smooth curve. Further, the forming, shaping, configurating, and creating steps, optionally include: forming the base portion, the base lead portion, and at least one additional lead to be substantially flat and parallel; notching the base portion at the edges where the one or more additional leads are to be installed, to provide ready access of a bending tool; installing and connecting at least one semiconductor chip; bending the leads preparatory to encapsulation; and/or molding a protective encapsulant of predetermined controlled shrinkage around the side portion, the first surface, the semiconductor chip, and a portion of the leads so that the second surface of the base portion and the terminal portions of the leads remain exposed.

DETAILED DESCRIPTION OF THE DRAWINGS

Figure 1A:
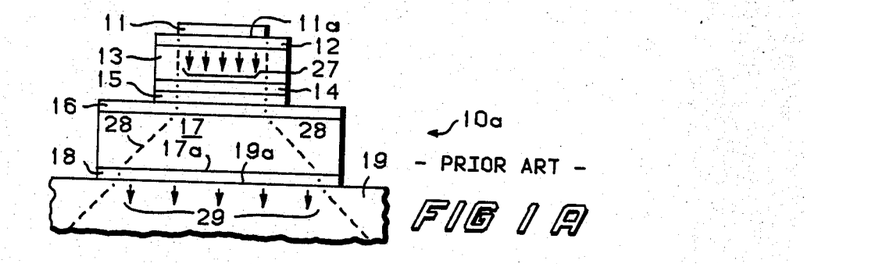
FIGS. 1A-B show, in schematic form and according to the prior art, the thermal path between a semiconductor chip and the external heat sink, through a metallic heat spreader, for two locations of an electrically isolating dielectric layer.
Figure 1B:
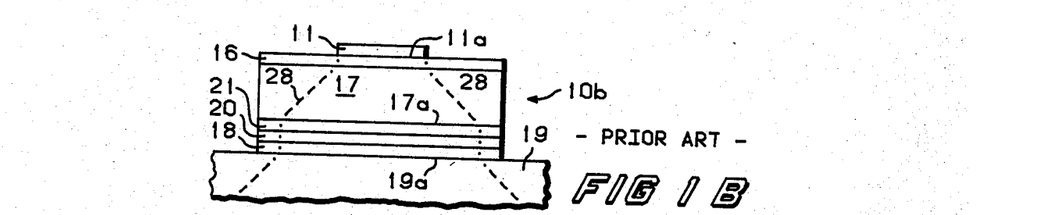

FIGS. 1A-B show, in schematic form, and according to the prior art, the thermal path between semiconductor chip 11 and external heat sink 19 for various locations of electric isolating layers. In FIG. 1A, device portion 10a has semiconductor chip 11 having heat transfer face 11a coupled to conductive heat spreader 17 by means of ceramic isolator 13. In order to bond the structure together it is necessary that ceramic isolator 13 have formed thereon metal layers 12 and 14 to provide adhesion to ceramic isolator 13. Heat spreader 17 optionally has thereon plating layer 16 for convenience in attaching metal coated ceramic isolator 13 by means of solder layer 15. Metallurgical and chemical bonds are formed between semiconductor device 11, ceramic isolator 13, and heat spreader 17, by means of metal layers 12, 14, 15, and 16 respectively. Heat spreader 17 is in turn mechanically clamped to external heat sink 19. Because neither heat transfer face 17a of device portion 10a nor heat receiving face 19a of external heat sink 19 are perfectly flat, interfacial layer 18 exists between heat spreader 17 and external heat sink 19. Interfacial layer 18 exists in all devices which are only mechanically coupled to a heat sink. Thermally conductive greases can be used to reduce but not eliminate the thermal impedance of interfacial layer 18.

It will be readily apparent to those of skill in the art that the same quantity of heat flows across interface 11a out of semiconductor chip 11, as flows across interface 17a into receiving face 19a of external heat sink 19. Dashed lines 28 shows the approximate contour by which heat spreads as it passes through the several layers of the device and conductive heat spreader 17. Arrows 27 represent the heat flowing across interface 11a from semiconductor chip 11. Arrows 29 represent the same quantity of heat flowing across interface 17a into external heat sink 19. It will be readily apparent that the thermal flux (heat flow per unit area) is higher at interface 11. Because ceramic isolator 13 has a substantially higher thermal resistivity than conductive heat spreader 17 or metallic layers 12, and 14-16, locating ceramic isolator 13 between semiconductor chip 11 and heat spreader 17 results in the greatest thermal resistance for a given degree of electrical isolation. This is a significant disadvantage of many prior art devices which are built with the structure of FIG. 1A.

In FIG. 1B, showing device portion 10b, ceramic isolator 13 has been eliminated and semiconductor device 11 is bonded directly to optional plating layer 16 of heat spreader 17. To obtain electrical isolation, flexible dielectric 20 is mechanically inserted between heat spreader 17 and external heat sink 19. Mica and insulating plastics are examples of materials used for layer 20. Since no metallurgical or chemical bond exists between layer 20 and heat spreader 17, additional interfacial layer 21 exists between heat spreader 17 and isolation layer 20. It is common to use organic greases between isolation layer 20, and heat spreader 17, and external heat sink 19. While the configuration of FIG. 18 provides thermal performance equivalent to or improved over the performance of configuration of FIG. 1A, it suffers from the disadvantage that the user must install layer 20 while mounting device 10b on external heat sink 19. Since thin plastic or mica sheets are relatively fragile, this is not a desirable feature.

Figure 2:
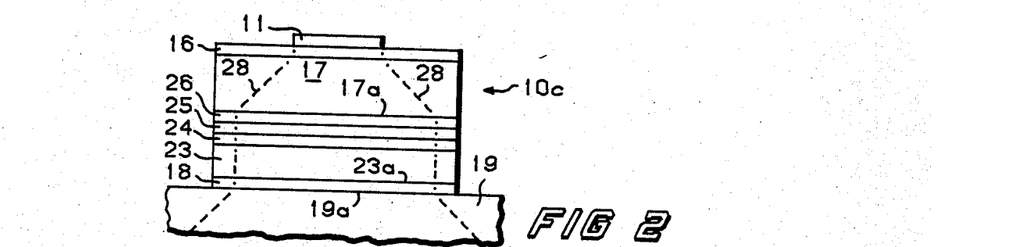
FIG. 2 shows, in schematic form and according to the present invention, the thermal path between a semiconductor chip and the external heat sink for a ceramic isolator brazed or soldered to the outer face of the heat sink.

In FIG. 2 showing device portion 10c, semiconductor device 11 is coupled to heat spreader 17 by optional plated layer 16. Heat spreader 17 has optional plated layer 26 to facilitate bonding of ceramic isolator 23. Ceramic isolator 23 has metal coating 24 to facilitate metallurgical bonding of isolator 23 to heat spreader 17 by means of solder layer 25. Ceramic isolator 23 is thus permanently bonded to heat spreader 17 and interface 23a forms the heat transfer face of the finished device. The configuration of FIG. 2 is superior to FIG. 1B in that the user does not have to handle separate isolation layer 20, and is superior to the configuration of FIG. 1A in that the ceramic isolator is placed in the thermal circuit at the point of minimum rather than maximum thermal flux. However, the structure of FIG. 2 is complex and expensive to manufacture. Also, as the area of heat spreader 17 is made larger, the thickness of ceramic isolator 23 must be increased in order to avoid breakage. This increases the thermal impedance of the package.

Figure 3:
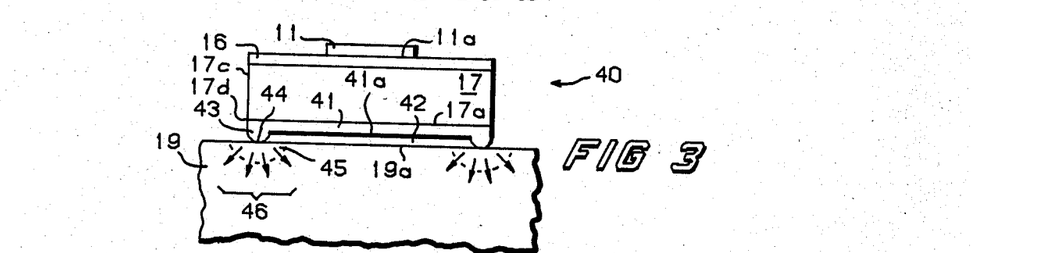
FIG. 3 shows in schematic form the internal construction and thermal pathway between a semiconductor die and an external heat sink when a glassy ceramic or porcelain layer, according to the present invention, is used on the outer face of an ordinary metallic heat spreader to provide electrical isolation.

As shown in FIG. 3, according to the present invention, substantially simpler structure 40 can be constructed by replacing ceramic isolator 23 and associated metal bonding layers 24–26 by glassy dielectric layer 41 which is bonded directly to interface 17a of heat spreader 17. It was found, however, that when the glassy dielectric materials were applied directly to conventional heat spreader 17, that ridge 43 of glassy material forms at periphery 17d of conventional heat spreader 17. Ridge 43 prevents heat transfer face 41a from contacting heat receiving face 19a of external heat sink 19 over a significant area. Gap 42, of appreciable thickness, is created between heat transfer face 41a and heat receiving face 19a. Direct thermal contact exists only at a line corresponding to peak 44 of ridge 43. Heat is directly coupled to external sink 19 through relatively small portion 45, as indicated by arrows 46. Heat also flows across gap 42, but less effectively.

Figure 4:
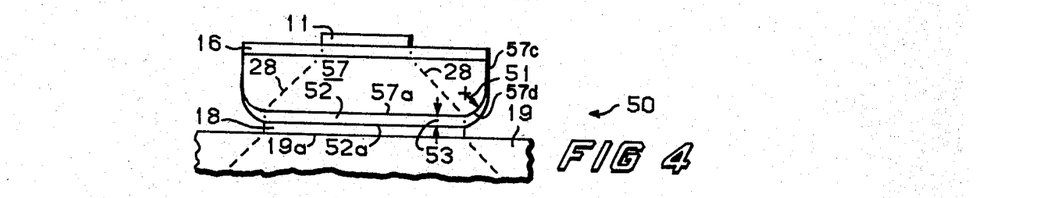
FIG. 4 shows in schematic form the internal construction and thermal pathway, according to the present invention, between a semiconductor die and an external heat sink when a glassy ceramic or porcelain layer is used to provide electrical isolation on a metallic heat spreader of improved design.

This difficulty was overcome by changing the heat spreader configuration to that shown in FIG. 4. Device portion 50 of FIG. 4, according to the present invention, has semiconductor die 11 mounted directly on optional plated layer 16 of heat spreader 57. Heat spreader 57 differs from heat spreader 17 of FIG. 3 in that peripheral corner 17d between heat transfer surface 17a and side portion 17c of heat spreader 17 has been replaced by substantially smooth curved surface 57d connecting heat transfer face 57a and side portion 57c of improved heat spreader 57. Substantially smooth curved surface 57d has minimum radius of curvature 51. Glassy dielectric film 52 is applied substantially on surface 57a and smooth curved surface 57d of improved heat spreader 57. Glassy dielectric 52 has thickness 53 and external heat transfer face 52a. It is not necessary that substantially smooth curved surface 57d has only a single radius of curvature, that is, conform to the arc of a single circle. It may be a more complex curve having a range of radii of curvature, in which case radius of curvature 51 represents the minimum radius of curvature of any portion of substantially smooth curved surface 57d.

It has been discovered that when minimum radius of curvature 51 is made equal to or larger than thickness 53 of glassy dielectric layer 52 that ridge 43 substantially does not form. While minimum radius of curvature 51 must be at least equal to thickness 53 it is desirable that larger radii be used, two to three times thickness 53 being convenient. Larger values are also useful. Having radius 51 equal or greater than twice thickness 53 also increases the chip resistance of the glassy dielectric layer on curved surface 57d, since the larger radius distributes the force of impact blows over a larger area. This provides improved mechanical ruggedness.

Substantially smooth curved surface 57d may be formed by any convenient means such as machining, rolling, stamping, coining, etching, or equivalent. The structure of FIG. 4 is simpler and less costly to manufacture than prior art structures and gives equal or superior thermal performance due to the elimination of several layers. Additionally, glassy dielectric isolation layer 52 of FIG. 4 may be made substantially thinner than ceramic isolator 23 of FIG. 2 or plastic isolator 20 of FIG. 1B since it need not be handled in a free standing form. Other things being equal, this provides an additional improvement in the thermal performance of the package.

Figure 5A:
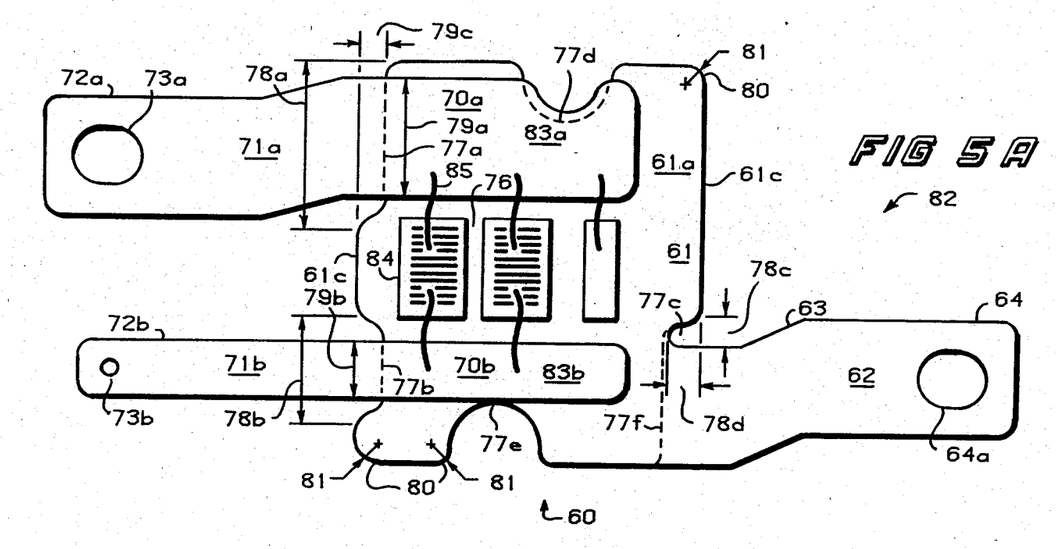
FIGS. 5A-B show the internal construction details and initial piece part arrangement of a power device, according to the present invention.
Figure 5B:
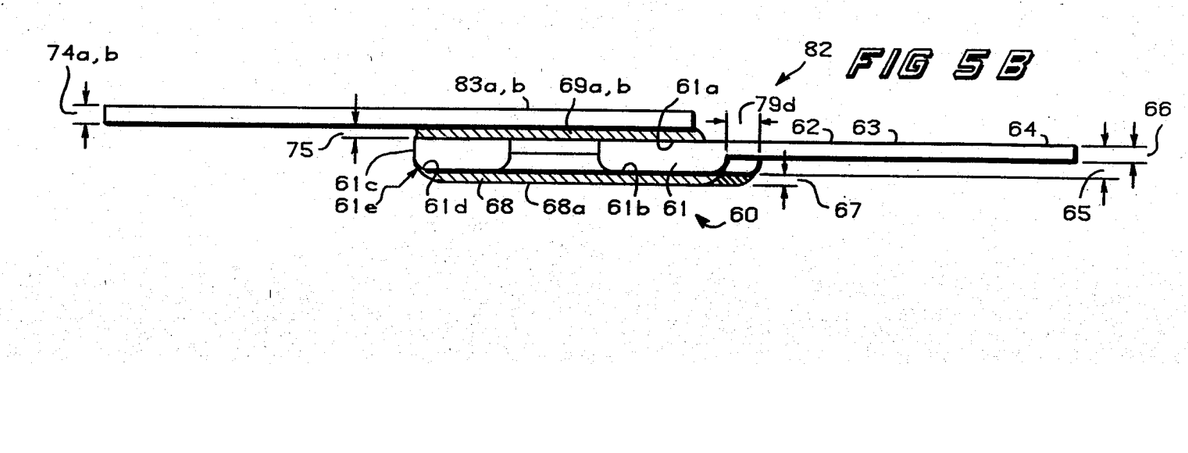

FIGS. 5A–B show the internal construction details and initial piece part arrangement of a power device package, according to the present invention. Metallic heat spreader and piece part 60 has base portion 61 of first predetermined thickness 65, and base lead portion 62 of second predetermined thickness 66. Base portion 61 has first surface 61a, opposed second surface 61b, and side portion 61c substantially coupling first surface 61a and second surface 61b. Side portion 61c and second surface 61b are joined by substantially smooth curved surface 61d. As with surface 57d of FIG. 4, substantially smooth curved surface 61d of FIGS. 5A–B has predetermined minimum radius of curvature 61e. Second surface 61b and substantially smooth curved surface 61d of FIG. 5A–B have coated thereon glassy dielectric layer 68 of predetermined thickness 67. Thickness 67 must be sufficient to provide the desired amount of electrical isolation. Thicknesses in the range 100 to 300 μm are useful for devices having isolation voltage ratings up to several thousand volts. Thinner and thicker layers may be used depending on the voltage rating. However, the thermal impedance increases with increasing thickness.

Metallic heat spreader 60 has extending therefrom base lead portion 62 having extension portion 63 and terminal portion 64 containing, optionally, connection hole 64a. It will be recognized by those of skill in the art that base lead portion 62 may be an integral part of heat spreader 60, or formed separately and attached to base portion 61. Metallic heat spreader 60 has mounted thereon, by electrically insulating means 69a–b, additional leads 70a–b having extension portions 17a–b and terminal portions 72a–b, with optional connection holes 73a–b. Leads 70a–b have thicknesses 74a–b respectively. Thicknesses 74a–b need not be the same. Insulating means 69a–b have thicknesses 75a–b associated respectively with leads 70a–b. While two additional leads 70a–b have been shown, it will be recognized by those of skill in the art that more or less can be used. First surface 61a of base portion 61 of metallic heat spreader 60 has device mounting portion 76.

Base portion 61 has formed therein several notches 77a–e. Notches 77d–e provide for the passage of the mounting screws which will eventually hold the encapsulated device to an external heat sink. In the finished device the mounting screws do not contact base portion 61 or leads 70a–b. Notch 77c, having width 78c and depth 78d, facilitates bending base lead potion 62. Base portion 61 is relieved at 77f for distance 79d to provide access for a bending tool to permit bending of base lead portion 62 without cracking glassy dielectric coating 68 on surfaces 61b and 61d of base portion 61. Distance 79d is desirably at least twice thickness 66. Dimensions 78c–d are desirably at least equal to thickness 66. Notches 77a–b are located beneath extension portions 71a–b of additional leads 70a–b. Notches 77a–b have widths 78a–b, respectively, which equal or exceed widths 79a–b of extension portion 71a–b of additional lead 70a–b. Depth 79c of notches 77a–b provides access for a bending tool so that extension portions 71a–b may be bent without damaging insulating means 69a–b which attach leads 70a–b to base portion 61. Depth 79c is desirably at least twice thickness 74a or 74b respectively of additional leads 70a–b.

Side 61c has along its lengths various corners and bends 80 having minimum radii of curvature 81 in the direction of the length of side 61c. It is essential that minimum radius of curvature 81 be equal to or greater than thickness 67 of glassy dielectric layer 68, and preferably substantially larger. It has been found convenient that minimum radius of curvature 81 of side 61c be approximately one to four times thickness 65.

Piece part assembly 82 of FIGS. 5A–B is conveniently fabricated by first punching out metallic heat spreader piece part 60 comprising base portion 61 and base lead portion 62, as well as additional lead piece parts 70a–b. Base lead portion 62 may be formed in the same operation as base portion 61, or may be formed separately and attached by any convenient electrically conductive means to side 61c or surface 61a. Heat spreader piece part 60 and lead piece parts 70a–b are conveniently made of copper or copper alloys. However, other metals such as iron, steel, aluminum, aluminum alloys, and combinations thereof with or without copper or copper alloys, and with or without surface platings will suffice. Other metals and combinations of metals are also useful.

While punching is a convenient means of cutting out piece parts 60 and 70a–b, and simultaneously trimming them to the configurations shown in FIGS. 5A–B, other methods such as etching, machining, sawing, or the like will suffice. Simultaneous with or subsequent to punching out piece part 60, substantially smooth curved surface 61d joining side portion 61c and second surface 61b is conveniently formed. Substantially smooth curved surface 61d may be formed by stamping, rolling, coining, etching, machining, polishing, or the like. It is convenient to form substantially smoooth curved surface 61d in the same operation in which piece part 60 is created. Methods for punching, forming, stamping, etching, machining, sawing, rolling, coining, and/or polishing are well known in the art. Notches 77a–e and relief 77f are formed conveniently coincident with or subsequent to the formation of piece part 60. Rounded curves and corners 80 having minimum radius of curvature 81 are conveniently formed in a similar manner. Care should be taken that second surface 61b of base 61 is substantially flat and smooth. It need not be polished.

Subsequent to the mechanical shaping of metallic heat spreader piece part 60, second surface 61b and substantially smooth curved surface 61d of base portion 61 of metallic heat spreader piece part 60 are coated with glass forming dielectric material. The glass forming dielectric material must be intimately bonded to surfaces 61b and 61d. As used herein, "intimately bonded" means chemically bonded by comparatively strong ionic and/or covalent chemical bonds as opposed to weaker Van der Waals bonds or mechanical attachment.

The glass forming dielectric material is conveniently applied in the form of a slurry of glass frit of a predetermined and substantially uniform thickness, and then dried. The glass frit is fused and intimately bonded to surfaces 61b and 61d by heating. Heating can be performed contemporaneously, or more conveniently, performed later as part of the fabrication of assembly 82. Other means for forming adherent, intimately bonded, glassy dielectric layers can also be used. It is important that outward facing surface 68a of glassy dielectric layer 68 be substantially smooth and flat. As used herein, the words "refractory dielectric means" encompass "glassy dielectric" and "glass forming dielectric"; these terms being intended to include electrically insulating glasses, ceramics, porcelains, and other refractory dielectrics. It is desirable that the glassy dielectric material has a thermal conductivity exceeding about 0.8 $Wm^{-1}K^{-1}$ at 25° C. Glass frit type L-1 and/or type 1851, manufactured by Ferro Co. of Cleveland, Ohio are useful glass or porcelain dielectric materials for coating copper base portions. Other copper sealing glasses will also serve. It will be recognized by those of skill in the art that the adherence of glasses, porcelains and/or ceramic layers to metal surfaces, such as heat spreader 57 or 60, is improved by surface pretreatments such as oxidation or borating. These techniques are well known in the art. Surface 61b is conveniently oxidized or borated before applying glassy dielectric 68.

Piece part assembly 82 is conveniently fabricated by placing additional leads 70a–b in a boat, and placing preforms of insulating attachment means 69a–b, typically also a glassy dielectric material on portions 83a–b of leads 70a–b. Metallic heat spreader 60 is then placed in the same boat so that surface 61a contacts the glass preforms placed on portions 83a–b of additional leads 70a–b, the boat providing the necessary alignment to properly position piece parts 60 and 70a–b with respect to each other. In this configuration, glassy dielectric layer 68 faces away from the other piece parts. The boat containing the assembled piece parts is then heated in a controlled atmosphere. Non-oxidizing atmospheres are desirable, with nitrogen or forming gas being suitable. Temperatures in the range of 600°–1000° C. are useful with 650°–900° C. being preferred. The assembly is maintained at the elevated temperature for sufficient time to provide fusion and intimate bonding of the glassy materials to the piece parts. The fused glass preforms provide insulating means 69a–b which bond leads 70a–b to base portion 61. The fused glass on surfaces 61b–d provides glassy dielectric coating 68 of substantially uniform thickness 67. It will be recognized by reference to glassy dielectric layer 52 of FIG. 4, that glassy dielectric layer 68 of FIGS. 5A–B also tapers to substantially zero thickness at approximately the point where substantially smooth curved surface 61d joins side 61c, although this is not critical.

Piece part assembly 82 now forms a substantially rigid and flat structure which is readily handled so that semiconductor chips 84 may be optionally bonded to device bonding portion 76 of surface 61a of base portion 61. Semiconductor die 84 are connected to additional leads 71a–b by wire bonds 85. It will be recognized by those of skill of in the art that a wide variety of means may be used to connect semiconductor chips 84 to leads 70a–b. Similarly, a wide variety of methods may be used to attach semiconductor die 84 to base portion 61. Furnace soldering has been found to be a convenient die attachment means.

Lead extension portions 63, and 71a–b are then mechanically formed at substantially right angles to the plane of base portion 61. Notches 77a–b provide convenient access for gripping lead portions 71a–b, and relief 77f for gripping lead portion 63, so that forming may be accomplished without damaging insulating means 69a–b or glassy delectric layer 68. Formed assembly 82 is then placed in a mold and encapsulated so that surface 68a of glassy dielectric 68 on surface 61b of heat spreader 60, and terminal portions 64 and 72a–b remain exposed from the encapsulant (see FIGS. 6A-B). The encapsulated device may then be conveniently tested. It is also convenient to additionally form terminal portions 64 and 72a so that they retain capture nuts 91a–b as shown in FIG. 6A.

Figure 6A:
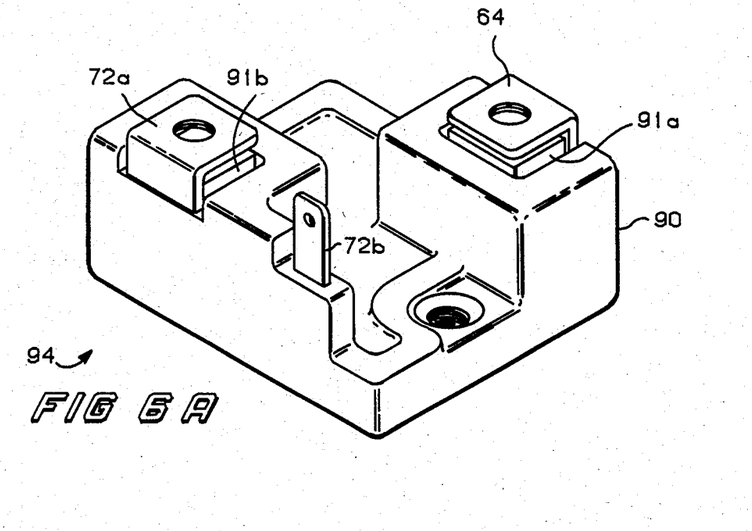
FIGS. 6A-B show a power device utilizing the piece parts of FIGS. 4A-B after encapsulation and according to the present invention.
Figure 6B:
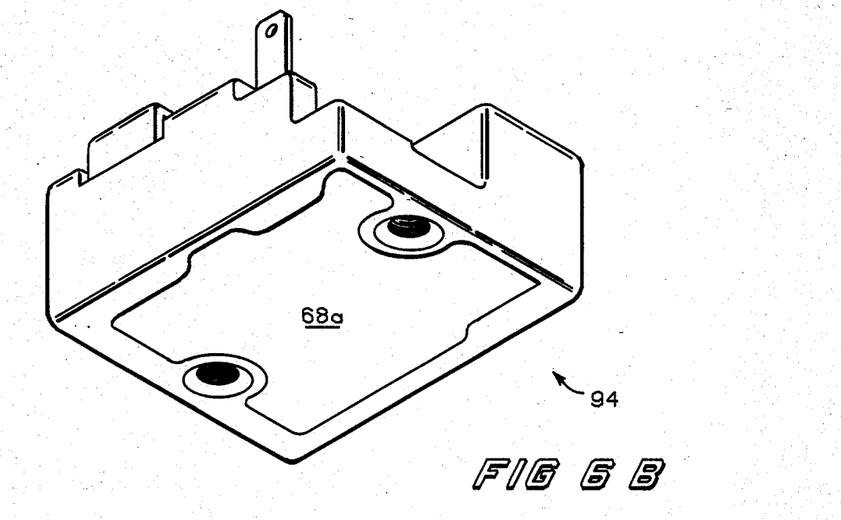

The device of FIGS. 6A-B has a substantially rectangular shape, although other configurations are possible. Terminal portions 64 and 72a are arranged on the diagonal of the package, well separated from each other and terminal portion 72b. It will be recognized by those of skill in the art that this arrangement is convenient for providing the minimum terminal spacings established by the Underwriters Laboratories in Bulletin UL508 dated Aug. 19, 1979 for components for use in industrial environments.

FIGS. 6A-B show substantially finished power device 94 utilizing piece parts 82 of FIG. 5A-B, according to the present invention and encapsulated with encapsulant 90. FIG. 6B is a bottom view of FIG. 6A in which may be seen exposed, surface 68a of glassy dielectric layer 68 on surface 61b. Surface 68a forms the heat transfer surface of the finished device. It is important that encapsulant 90 have a predetermined controlled mold shrinkage and coefficient of expansion, so that base portion 61 is substantially not deformed by contraction/expansion of encapsulant 90 during or after molding. It has been discovered that filled polyimide materials with a molding shrinkage factor of less than 0.25% are satisfactory, with less than 0.2% preferred. The molding shrinkage factor corresponds to the percent shrinkage from mold to molded dimensions, measured as specified in ASTM Method D-955-51 (Reapproved 1969). Desirable filler materials are 50–70% fused quartz and 10–20% soda-lime glass (E-glass), totaling 60–80%, and the balance polyimide. Other refractory dielectric filler material will also serve. Type 600 polyimide, supplied by Rhone-Poulenc of Paris, France is useful. Other polyimides will also serve.

Figure 7A:
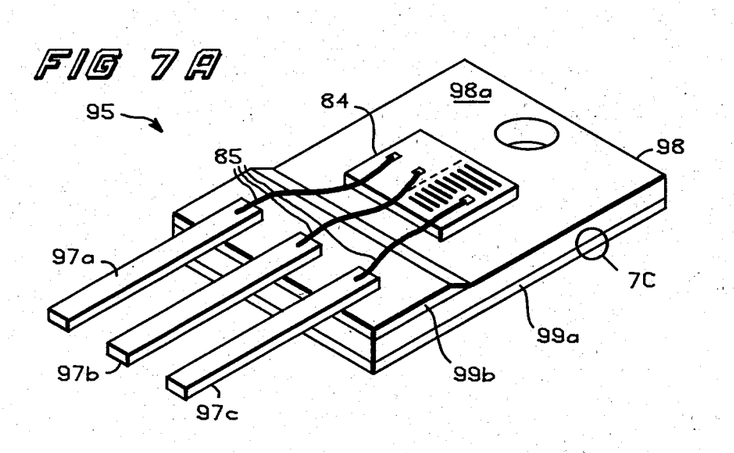
FIGS. 7A-C show an alternative embodiment of a power device package and power device according to the present invention.
Figure 7B:
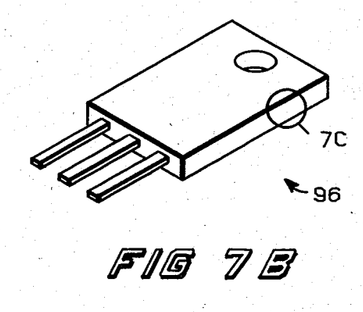
Figure 7C:
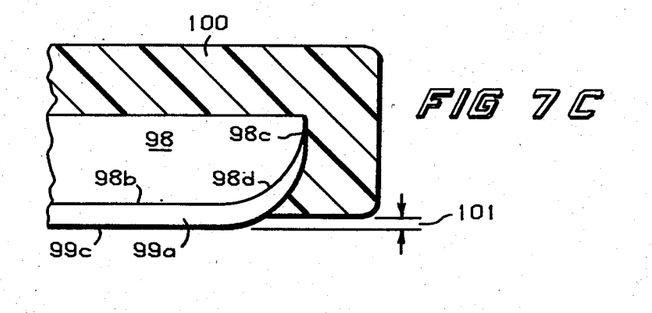

FIGS. 7A-C show an alternative embodiment of a power device package according to the present invention. In FIG. 7A, piece part subassembly 95 comprises metallic heat spreader 98 having first surface 98a on which is mounted semiconductor die 84, coupled to external leads 97a–c by means of wire bonds 85. Leads 97a–c are isolated from metallic heat spreader 98 by insulating means 99b. Metallic heat spreader 98 (FIG. 7C) has second surface 98b, side 98c, and substantially smooth curved surface 98d joining side 98c to second surface 98b. Substantially smooth curved surface 98d and second surface 98b are substantially coated by glassy dielectric layer 99a. Piece part assembly 95 is coated with encapsulant means 100 to form substantially finished device 96 of FIG. 7B-C. Heat transfer surface 99c protrudes from encapsulant means 100 by predetermined amount 101, so that surface 99c can engage an external heat sink without interference from encapsulant means 100.

The device of FIG. 7A-C is formed by placing leads 97a–c in a boat or holder, adding heat spreader 98, precoated with glassy (or glass forming) layers 99a–b and heating in a manner substantially similar to those described in connection with the device of FIGS. 5A-B and 6A-B.

It will be apparent to those of skill in the art that the present invention provides an improved semiconductor power device package and an improved semiconductor power device in which the external heat transfer face is electrically isolated from the semiconductor chip without the use of a dielectric spacer between the chip and the heat spreader. It will be further apparent that this improved device has been achieved by means of an insulating layer which is intimately bonded to the outward heat transfer face of the heat spreader, and that the structure and method does not require the use of separate external insulating means, and utilizes a minimum number of piece parts. It will be further apparent that the finished device has a substantially flat and smooth heat transfer face and is mechanically rugged and well adapted to the industrial environment. It will be additionally apparent that the flat configuration and substantially parallel initial relationship of the piece parts provides a particularly convenient arrangement for the improved manufacture of power device packages and power devices. It will be further apparent that an improved method has been provided for the manufacture of semiconductor power device packages and semiconductor power devices having the desired structural features described herein.

While the present invention has been described in terms of particular structures and materials it will be apparent to those with skill in the art that these concepts apply to a wide range of devices and structures, in particular, the use of different metals for the piece parts, the use of a variety of glassy materials and preparation methods (e.g. plasma spraying) for the dielectric layers, the use of other encapsulant materials also having the desired controlled shrinkage factor, and the use of a variety of mechanical techniques for shaping and assembling the piece parts. Accordingly, it is intended to encompass all such variations as fall within the spirit and scope of the present invention.

We claim:

1. A method for manufacturing an electrical device adapted to receive at least one semiconductor die, comprising:

forming a metallic heat spreader having a base portion with a first surface adapted to receive semiconductor die, a second surface opposite said first surface adapted to receive refractory dielectric coatings, and a side portion coupled to said first and second surfaces;

forming a base lead portion extending from said base portion of said metallic heat spreader;

shaping said metallic heat spreader so that said base portion has a first thickness and said base lead portion has a second thickness;

configuring said base lead portion so that it has a first extension portion ending in a first terminal portion;

creating a substantially smooth surface on said metallic heat spreader having a predetermined minimum radius of curvature and joining said side portion and said second surface;

coating said second surface and a portion of said substantially smooth curved surface with a refractory dielectric of predetermined thickness chemically bonded to said second surface, and said substantially smooth surface;

regulating said thickness of said refractory dielectric coating to be less than said predetermined minimum radius of curvature; and attaching to said first surface of said base portion, by electrically insulating means, at least one additional lead having a second extension portion ending in a second terminal portion.

2. The method of claim 1 further comprising regulating said thickness of said refractory dielectric coating to be less than one-half said predetermined minimum radius of curvature.

3. The method of claim 1 further comprising installing at least one semiconductor chip, bending said base lead and at least one additional lead, and molding a protective encapsulant around said side, said first surface and a portion of said leads so that said terminal portions of said leads and a portion of said refractory dielectric coated on said second surface remain exposed.

4. The method of claim 3 further comprising using for said protective encapsulant a material having a molding shrinkage factor of less than 0.25%.

5. The method of claim 4 wherein said protective encapsulant material is a filled polyimide plastic containing 50–70% quartz and 10–20% glass.

6. The method of claim 1 further comprising notching throughout its thickness said base portion of said metallic heat spreader during one of said forming, shaping, configuring, or creating steps, placing said notches in said side portion at locations above which said extension portion of said at least one additional lead pass and adjacent to said base lead portion, and cutting said notches to a depth into said base portion not less than the thickness of said base portion.

7. The method of claim 1 wherein said coating step comprises applying a glass forming material and heating to fuse and intimately bond said glass forming material to said second surface and said substantially smooth curve.

8. The method of claim 1 wherein said forming, shaping, configuring and creating steps comprise forming said base portion, said base lead portion and said at least one additional lead to be substantially flat, and assembling said base portion, said base lead portion, and said at least one additional lead in a substantially parallel arrangement.

* * * * *